United States Patent [19]

Franks

[11] Patent Number: 5,776,298

[45] Date of Patent: Jul. 7, 1998

[54] TISSUE PREPARATION APPARATUS AND METHOD

[76] Inventor: James W. Franks, 2153 Driftwood Cir., Palm Beach Gardens, Fla. 33410

[21] Appl. No.: 690,298

[22] Filed: Jul. 26, 1996

[51] Int. Cl.$^6$ .................... B29B 13/04; B29B 11/02
[52] U.S. Cl. .................... 156/390; 83/915.5; 156/80; 156/498; 264/28; 269/254 MW; 269/257; 269/909
[58] Field of Search .................... 264/28, 135; 156/57, 156/80, 498, 390; 269/257, 909, 254 MW; 83/915.5

[56] References Cited

U.S. PATENT DOCUMENTS

| | | | |
|---|---|---|---|
| 3,204,424 | 9/1965 | McCormick | 83/915.5 X |
| 3,218,896 | 11/1965 | McCormick | 83/915.5 X |
| 3,552,733 | 1/1971 | Pickett | 83/915.5 X |
| 4,012,475 | 3/1977 | Kindel | 83/915.5 X |
| 4,248,821 | 2/1981 | Van Dellen | 264/135 |
| 4,545,831 | 10/1985 | Ornstein | 156/57 |
| 4,569,647 | 2/1986 | McCormick | 422/99 X |
| 4,695,339 | 9/1987 | Rada | 156/80 |
| 4,752,347 | 6/1988 | Rada | 83/915.5 X |
| 5,416,029 | 5/1995 | Miller et al. | 436/176 |
| 5,452,584 | 9/1995 | Diggs | 62/64 |

OTHER PUBLICATIONS

C. Hanke, M. Lee, "Cryostat Use and Tissue Processing in Mohs Micrographic Surgery", Jan. 1989, pp. 29–32, *J. Dermatol. Surg. Oncol.*, vol. 15 No. 1.

D. Gormley, "Evaluation of a Method for Controlled Tissue Embedding for Histologic Evaluation of Tumor Margins", 1987, pp. 308–315, *Am. J. Dermatopathol.*, vol. 9 No. 4.

J. Concepcion, "Letters to the Editor—How to Prepare Tissue Blocks", Feb. 1986, pp. 112–113, *J. Dermatol. Surg. Oncol.*, vol. 12 No. 2.

N. Honda, D. Friedman, "A Simple Method of Tissue Embedding for Mohs Micrographic Surgery", May 1989, pp. 502–504, *J. Dermatol. Surg. Oncol.*, vol. 15 No. 5.

C. Hanke, H. Menn, J. O'Brian, "Chemosurgical Reports: Frozen–Section Processing with the Miami Special", Apr., 1983, pp. 260–262, *J. Dermatol. Surg. Oncol.*, vol. 9 No. 4.

V. Carter, "A New Method for Preparing Tissue Blocks for Cryostat Sectioning", Jul. 1985, pp. 687–689, *J. Dermatol. Surg. Oncol.*, vol. 11 No. 7.

Reference Manual. *AO Reichert Model 975C and 976C Histostat™ Cryostat Microtome*, 1984, pp. 7–9.

Operations Manual, *Cryo Hist*, Date Unknow, pp. 1–15.

R. Motley, P.Holt, "A simple device for optimal tissue preparation for Mohs micrographic surgery", 1992, pp. 57–59, *British Journal of Dermatology*, vol. 126.

B. Leshin, S. Cook, D. Frye, "Cryomold: A Device for Tissue Embedding in Mohs Micrographic Surgery", 1991, pp. 234–236, *J. Dermatol. Surg. Oncol.*, vol. 17.

G. Koehn, "A New Modification for Preparing Tissue Blocks for Cryostat Sectioning", 1992, pp. 485–486, *J. Dermatol. Surg. Oncol.*, vol. 18.

M. Dogan, S. Snow, J. Lo, "Rapid Skin Edge Elevation Using the OCT Compound Droplet Technique to Obtain Horizontal Microsections in Mohs Micrographic Surgery", 1991, pp. 857–860, *J. Dermatol. Surg. Oncol.*, vol. 17.

(List continued on next page.)

*Primary Examiner*—Jeffery R. Thurlow

[57] ABSTRACT

An apparatus for mounting a tissue specimen on a chuck for sectioning in a cryostat including a base, a clamp for receiving a tissue preparation slide, a chuck holder secured to the base for holding the chuck in a predetermined orientation relative to the clamp, a support secured to the base and extending therefrom and terminating in a distal end, and, means for slideably securing said clamp to said support. The clamp is positionable between a first location in which the clamp is at a minimum distance from the chuck holder and a second location in which the clamp is at a maximum distance from the chuck holder. A method for using the apparatus is likewise disclosed.

13 Claims, 8 Drawing Sheets

OTHER PUBLICATIONS

W. Soohoo, B. Ruebner, P. Vogt, D. Wiese, "Orientation of Small, Flat, Frozen–Section Specimens", 1988, pp. 573–574, *Am. J. Surg. Pathol.*, vol. 12, No. 7.

L. Miller, Z. Argenyi, D. Whitaker, "The Preparation of Frozen Sections for Micrographic Surgery", 1993, pp. 1023–1029., *J. Dermatol.Surg. Oncol.*, vol. 19.

H. Randle, J. Zitelli, D. Brodland, R. Roenigk, "Histologic Preparation for Mohs Micrographic Surgery", 1993, pp. 522–524, *J. Dermatol.Surg. Oncol.*, vol. 19.

TISSUE PREPARATION APPARATUS AND METHOD

TECHNICAL FIELD

This invention relates to the preparation of tissue samples for sectioning, and specifically to preparation for tissue sectioning incidental to the Mohs tissue surgical technique.

BACKGROUND ART

The Mohs tissue surgical technique, which was developed by Frederic E. Mohs of Madison, Wis., is a method of removing skin tumors such as cutaneous malignancies and certain major carcinomas, and evaluating sections (very thin slices) of the tissue under a microscope. In order for Mohs surgery to be successful, high quality horizontally cut frozen tissue sections must be produced and microscopically reviewed to determine whether any residual tumor has spread beyond the tissue sample.

The Mohs process begins with the excising of a tissue sample which includes the skin tumor. The tissue sample is then marked for orientation purposes, for example, by scoring with a scalpel and marking the sample immediately left or right of the score with ink, to allow the surgeon to determine where additional excisions must occur should the results of an inspection of a microscopic section of tissue sample indicate that the tumor has spread beyond the excised sample. If residual tumor is indicated by the microscopic inspection, additional tissue is excised, and the procedure is repeated until there are no indications that the tumor has spread beyond the excised tissue samples.

The surface of the excised tissue to be inspected is the curved, generally bowl-shaped surface that results from the passage of the scalpel below the surface of the skin. This bowl-shaped surface must be converted to a planar surface in order to be sliced by a device known in the art as a microtome. The microtome is typically located in a refrigerated unit, called a cryostat, which is capable of maintaining an internal temperature of −20 degrees Celsius or below.

To enable this sectioning or slicing, the tissue must be mounted on a cryostat chuck with the flattened or planar surface exposed and perpendicular to the long axis of the cryostat chuck. The chuck and attached tissue sample are then placed into a chuck fixture in the cryostat where the tissue is cut into frozen sections having a thickness of only five to seven micrometers. Each section is then placed on a microscope slide and the section is stained by dipping the slide in solvents and various dye solutions. After the desired amount of staining is achieved, a clear glue-like substance is used to attach a thin layer of glass called a "cover slip".

The dye causes cell walls, cell contents, and also extracellular material within the section, which would normally appear transparent, to be readily visible when viewed under a microscope for the presence of malignant cells and also for a host of inflammatory reaction to those malignant cells. If the surgeon determines that carcinoma cells are present in the section, further excision of tissue from the patient is necessary.

As those skilled in the art will readily appreciate, if the first section does not include all of the formerly bowl-shaped surface, which may occur if the planar surface is not parallel to the path of relative movement between the cryostat knife and the tissue sample, then the surgeon must review subsequent deeper sections until a determination can be made that all of the formerly bowl-shaped surface has been evaluated. This can be a time consuming effort, since each section must be stained and microscopically examined and interpreted by the surgeon before a determination can be made as to whether further excision of tissue is necessary. Therefore, orientation of the mounted tissue sample so that the planar surface is parallel to the path of the cryostat knife is key to ensuring that the cutting time involved in sectioning the tissue sample will be a minimum, since that means that the first tissue section may be the only one that the surgeon needs to evaluate.

The prior art discloses various methods and/or devices which attempt to solve this problem of flattening the bowl-shaped surface to obtain a perfect section (as defined herein below). The first method, referred to as the American Optical Heat Extractor, involves use of a copper jig to hold a cryostat chuck, and a solid metal cylinder which is movably attached to the jig. (This type of jig and metal cylinder was initially offered on cryostats manufactured by American Optical, and currently standard equipment on most cryostats regardless of the manufacturer.) The jig, chuck and cylinder are maintained at cryostat temperatures (−20 degrees C.), and O.C.T. fluid (a clear, tissue mounting fluid such as this is sold under the brand name Tissue Tek II O.C.T. Compound, by Miles Laboratories, Inc.) is placed onto the tissue mounting surface of the chuck. (The O.C.T. has the general consistency and viscosity of egg whites, and freezes at a temperature below that at which the tissue samples freeze.) A tissue sample is then immediately placed onto the liquid O.C.T. with the bowl-shaped surface facing away from the tissue mounting surface of the chuck. The metal cylinder is then lowered onto the tissue sample, sandwiching the specimen between the chuck and the metal cylinder and extracting heat from both the tissue specimen and the O.C.T. After 30 seconds or so when both the tissue specimen and the O.C.T. are frozen, the cylinder is somehow jarred to free it from the tissue specimen and the O.C.T., leaving the tissue specimen and the O.C.T. frozen to the chuck. Once frozen, the O.C.T. acts as a glue by bonding the tissue to the chuck, and also surrounding and supporting the tissue sample so it can be subsequently sliced by the microtome within the cryostat. Unfortunately, the first tissue section produced using this method often fails to include the complete periphery of the tissue specimen, requiring the review of multiple sequential tissue sections to ensure that no tumor is present on the formerly bowl-shaped surface.

A second method, referred to as the American Optical Tissue Presser, is a variation on the American Optical Heat Extractor, but includes a spring that partially supports the metal cylinder so that the full weight of the cylinder does not rest on the tissue specimen. Unfortunately, this method also often fails to produce first tissue sections which include the complete periphery of the tissue specimen. Accordingly, the review of multiple sequential tissue sections to ensure that no tumor is present on the formerly bowl-shaped surface is often required.

A third method, referred to as the Bard Parker scalpel handle method, involves freezing the tissue specimen to the chuck while using the flat handle of a metal scalpel to flatten the bowl shaped surface while the temperature drops. The surgeon moves the scalpel handle back and forth across the tissue sample and "eyeballs" the relative flatness of the bowl-shaped surface. The scalpel is removed before it has a chance to stick to the freezing O.C.T. and tissue sample. This line-of-sight method becomes less exact when the edges of the tissue sample curl under or sink lower than the back-and-forth path of the scalpel handle. As a result, this method also often fails to produce first tissue sections which include the complete periphery of the tissue specimen.

A fourth method, referred to as the glass slide method, is the same as the Bard Parker scalpel handle method, except that a glass microscope slide is substituted for the scalpel handle. Alternately, the tissue specimen may be frozen to the glass slide, a drop of O.C.T. placed on the tissue, and then the slide is inverted and frozen to the chuck using the line-of-sight method. A fifth method, referred to as the forceps method, is the same as the Bard Parker scalpel handle method, except that a forceps handle is substituted for the scalpel handle. Both the fourth and fifth methods suffer from the same reliance on the "eyeball" method of the Bard Parker method, and accordingly, each method also often fails to produce first tissue sections which include the complete periphery of the tissue specimen.

A sixth method, referred to as the Miami Special, involves a specially designed pair of pliers having a chuck holder attached to one jaw and a flat metal plate attached to the other jaw. The bowl-shaped surface of the tissue specimen is frozen to the flat metal plate, and then a tissue chuck with O.C.T. on the tissue mounting surface thereof is placed into the chuck holder with the tissue mounting surface of the chuck facing the tissue specimen. The jaws are then closed, sandwiching the tissue specimen and O.C.T. between the tissue mounting surface of the chuck and the flat metal plate. A coolant is then used to freeze the O.C.T., usually by immersing the end of the pliers holding the tissue sample in liquid nitrogen. While the Miami Special represents a significant improvement over the "eyeball" methods discussed above, the flat metal plate is only parallel to the tissue mounting surface of the chuck at one position of the jaws, and therefore the Miami Special almost always yields a flattened, formerly bowl-shaped surface that is at a slant relative to the tissue mounting surface of the chuck. Accordingly, the Miami Special also often fails to produce first tissue sections which include the complete periphery of the tissue specimen.

A seventh method involves use of a cryostat chuck, a polished metal disk, and a two-part metal jig. The bowl-shaped surface of the tissue sample is flattened by cooling the metal disk to −20 degrees Celsius and rolling the bowl-shaped surface against the metal disk. The tissue freezes to the metal disk which prevents return of the original bowl-shape, and the disk and tissue are placed in a cryostat to prevent thawing of the tissue. While the metal disk and attached tissue are maintained at a subfreezing temperature, a warm cryostat chuck is covered with O.C.T. fluid, and placed into a fixed portion of a jig located in the cryostat. When solidification of the O.C.T begins, the metal disk is placed in a mobile portion of the jig, and brought into apposition with the partially solidified O.C.T. compound by sliding the mobile portion of the jig onto the fixed portion of the jig, and allowing all components to stabilize at −20 degrees Celsius. The mobile jig is then removed, and the metal disk is "popped" off leaving the tissue sample on the cryostat chuck. An alternate version of this method involves the use of a nitrogen cooled, polished metal disk to eliminate the need to work within the confines of the cryostat when flattening the tissue sample.

An eighth method, involves a Cryomold, something akin to a clear, thin plastic envelope in the shape of an ice cube tray for a single cube. A thin layer of O.C.T. is added to the inside bottom of the Cryomold, which is then placed against the bowl-shaped surface of the tissue sample to be examined. The Cryomold is placed on the freezing bar within the cryostat, and, working within the confines of the Cryostat, the surgeon flattens the tissue sample with forceps as the O.C.T. and tissue sample freeze. Additional O.C.T. is then added to fill the Cryomold. The tissue chuck then is placed on the gelatinous surface, and the entire arrangement, including the tissue sample, is allowed to freeze in the cryostat. After freezing is complete, the plastic envelope is peeled away and the tissue sample is ready for sectioning.

One problem with the Cryomold is that, because the Cryomold is flexible, it must be remain on a hard, flat surface (such as the freezing bar in the cryostat) until the tissue sample has been flattened and frozen to the Cryomold with the O.C.T., and therefore actual freezing of the tissue sample to the bottom of the Cryomold cannot be directly observed. Since the O.C.T. on the bottom freezes uniformly, when the O.C.T. freezes at the positions where the peripheral edge is being held to the bottom, it is also freezing at those positions where the periphery is not being held to the bottom, so that when the surgeon seeks to freeze these other positions of the edge to the bottom, the O.C.T. has solidified and cannot be squeezed out, thereby supporting the edge off the bottom at these positions. When additional O.C.T. (at room temperature) is added to the Cryomold, the frozen tissue can thaw and curl at the peripheral edge, and due to the relatively large volume of O.C.T. which is required to fill the Cryomold, the freezing of the O.C.T. to the tissue chuck takes considerably longer than many other methods known in the art. If the tissue sample floats or curls into undesirable positions before complete freezing of the tissue sample and O.C.T. occurs, the tissue sample and O.C.T. must be thawed and the embedding process repeated until the tissue sample is frozen to the bottom of the Cryomold. Once frozen, the surgeon may raise the Cryomold from the freezing bar and view the bowl-shaped surface of the tissue sample to determine whether the entire periphery has been frozen to the inside bottom of the Cryomold. If the surgeon determines that the entire periphery of the bowl-shaped surface is not frozen to the bottom of the Cryomold, the tissue sample and O.C.T. must be thawed and the embedding process repeated until the entire periphery is visible. Since the Cryomold method uses O.C.T., which is clear (at room temperature, white when frozen), to bond the bowl-shaped surface of the tissue sample to the bottom of the Cryomold, it may not be readily apparent whether the entire periphery is located is a single plane as desired, or whether pockets of O.C.T. have lifted portions of the bowl-shaped surface off the bottom of the Cryomold. As a result of the foregoing, the surgeon may need to remove in excess of 300 microns of tissue before obtaining a perfect section.

In a ninth method, a variation of the American Optical Heat Extractor referred to as the cork method, a frozen tissue "well" is prepared by making a ring of O.C.T. compound around a rubber stopper on a glass slide at −20 degrees Celsius. Upon freezing of the O.C.T., the stopper is removed, and the bottom of the well is warmed with a fingertip and the excess O.C.T. is removed with a cotton swab. The excised tissue is placed into the well with the bowl-shaped surface facing the slide and allowed to freeze inside the cryostat at −20 degrees Celsius while a metal probe is used to press the bowl-shaped surface against the glass slide during the freezing process. After the tissue is completely frozen, the well is filled with additional O.C.T. and a metal heat sink is applied for approximately 3 minutes to speed the freezing process and help flatten the tissue. The frozen tissue sample is then gently pushed off the slide after warming the undersurface of the slide with the fingertips. The tissue sample is then inverted and mounted onto a metal chuck with additional O.C.T. and the heat extractor at −20 degrees Celsius for approximately 1 minute, and when broken away is ready for sectioning. When mounting the tissue sample to the grooved surface of the tissue chuck, the surface to be cut is visually aligned during freezing, again with the goal, often not attained, of mounting the flattened, formerly bowl-shaped surface of the specimen so that it is parallel to the grooved mounting surface of the tissue chuck.

A tenth method, referred to as the Motley method, uses a cylindrical chuck holder within a sleeve which is vertically oriented and slideably positioned thereabout. The chuck holder includes a pipe for delivering liquid nitrogen into the sleeve (from a source which is controlled by a foot-actuated valve), and vent holes for allowing the gaseous nitrogen to escape from within the sleeve. The top of the sleeve defines a plane which is parallel to the plane in which the tissue chuck is held by the chuck holder. A microscope slide is placed on the top of the sleeve so as to form a bridge, and the bowl-shaped surface of the tissue sample is pressed into contact with the slide with forceps while liquid nitrogen is sprayed on the opposite side of the slide via the pipe, thus freezing the tissue sample to the slide. The slide and sleeve are lifted away from the chuck holder, and a tissue chuck having O.C.T. thereon (at room temperature) is then placed in the chuck holder. The slide is then inverted (so that the tissue sample is now frozen to the lower surface of the slide) and the sleeve and slide are then placed back over the chuck holder and, using both hands to support the sleeve and hold the slide to the top thereof, the surgeon slides the sleeve down over the chuck holder until the tissue sample rests in the O.C.T. on the tissue chuck. The foot pedal is then actuated to spray liquid nitrogen against the underside of the chuck until the O.C.T. freezes. The surgeon's finger is then used to warm the slide until the tissue separates therefrom.

One drawback to the Motley method is that as the tissue sample is being pressed down onto the top side of the microscope slide, liquid nitrogen is sprayed against the bottom side, and so completeness of attachment of the tissue sample peripheral edge to the slide cannot be determined until the after the tissue sample is completely frozen and the slide can be flipped over and viewed, by which time frozen condensation will likely frost the slide, making inspection difficult. If inspection does reveal incomplete attachment, the tissue sample must be melted and the attachment process repeated. Slide breakage may occur due to the relatively large diameter of the sleeve and the force required to press some tissue samples flat against the slide, and because there is no seal between the microscope slide and the sleeve, escaping nitrogen gas blows out the top of the sleeve towards the surgeon and may splatter O.C.T. in the direction of the surgeon. Additionally, since the frozen tissue sample begins to warm as soon as the nitrogen spray ceases, time is of the essence in lowering the sleeve below the chuck holder, placing the chuck with O.C.T. thereon into the chuck holder, raising the sleeve, placing the slide with frozen tissue on top of the sleeve and lowering the sleeve until the tissue sample rests in the O.C.T. If this process takes too long, the tissue will melt away from the slide, and the chuck (with dripping O.C.T.) must be removed from the chuck holder and the process of freezing the tissue sample to the slide must be repeated. As the device is used, excess O.C.T. is likely to find its way between the chuck holder and the sleeve making raising and lowering of the sleeve more difficult. If the O.C.T. freezes to the sleeve and chuck holder, it may be impossible to remove the sleeve prior to removing the frozen chuck and tissue sample, making their removal difficult. If the O.C.T. freezes to the chuck and chuck holder, it may be impossible to remove the chuck from the chuck holder.

An eleventh method, referred to as the cooled embedding head, eliminates the need to operate within the confines of the cryostat by utilizing an embedding head having a polished, planar metal surface which is cooled by $CO_2$ to sub-freezing temperatures. The bowl-shaped surface of the tissue sample is flattened by manipulating the tissue to adhere to the cold metal of the polished surface so the once bowl-shaped surface is flattened down onto the head. With the tissue sample frozen to the embedding head, O.C.T. fluid is poured over the frozen tissue and, due to the temperature of the embedding head, the O.C.T. immediately begins to freeze. A tissue chuck received within a spring loaded tissue chuck holder and having a grooved mounting surface at room temperature is lowered by a system of levers, so that the grooved surface of the tissue chuck is brought into contact with the O.C.T. as is freezes. An additional nozzle through which $CO_2$ gas can be sprayed is directed at the tissue chuck to facilitate rapid cooling of the tissue chuck and freezing of the O.C.T. to the tissue chuck. When the O.C.T. solidifies, the plane of the tissue chuck is parallel to that of the polished, planar metal surface of the embedding head and the tissue which is adhering to it. If the O.C.T. sufficiently adheres to the grooved surface of the tissue chuck, then the attached tissue sample embedded in the O.C.T. is forcibly separated from the polished, planar metal surface of the embedding head. The chuck with frozen tissue is then placed in the cryostat for tissue sectioning.

One of the disadvantages of this latter method is that the surgeon has no way to determine whether the tissue sample is properly flattened against the embedding head until after the tissue sample is separated therefrom. Therefore, if for any reason the tissue sample failed to completely flatten against the embedding head (e.g. a crease is formed in the bowl-shaped surface during flattening of the sample, an air bubble is trapped between the embedding head and the tissue sample during the process of attaching the tissue sample to the embedding head, etc.), tissue sections cut from the tissue sample will not include the entire surface of the formerly bowl-shaped surface. If this situation goes undetected, the tissue section may not include cancerous material which was otherwise detectable. If the surgeon is somehow able to detect a crease or bubble in the tissue sample after freezing the tissue sample to the embedding head, the tissue sample must be thawed, rinsed and refrozen to the embedding head. However, such excessive thawing and refreezing of the tissue sample causes cell lysis, (breakage of the cell walls in the tissue sample and leakage of cell contents) which significantly changes the tendency of cells to absorb stain during the staining process described above, and gives cells a deflated and less defined architecture. This varied stain absorption and shrinkage of cells can make interpretation of the finished slides more difficult and error prone. Another disadvantage of this latter process is that once the O.C.T. is placed on top of the frozen tissue sample and embedding head, it immediately begins to cool, which leads to both condensation of humidity on the exposed surfaces of the O.C.T. and a dramatic increase in the viscosity of the O.C.T. As those skilled in the art will readily appreciate, the condensation becomes a frost which creates an interface between the tissue chuck and the O.C.T., and the increased viscosity reduces the tendency of the O.C.T. to flow into the voids of the textured surface of the tissue chuck, both of which may result in inadequate bonding of the O.C.T. to the tissue chuck and subsequent detachment of the tissue sample from the tissue chuck when the surgeon attempts to forcibly break away the frozen tissue sample and O.C.T. from the embedding head. Quickly lowering the tissue chuck onto the O.C.T. immediately after placing the O.C.T. on the embedding head can alleviate some of the effects of condensation and increased viscosity, but it may not allow adequate time for air present in the voids of the textured surface of the tissue chuck to escape, thereby preventing the O.C.T. from flowing into the voids and producing inadequate bonding of the O.C.T. to the chuck and the attendant problem described above. Likewise, placing an excess amount of O.C.T. on the embedding head and tissue sample while keeping the heat transfer rate of the embedding head constant will allow the surgeon a little more time for the O.C.T. to flow into voids of the textured surface of the tissue chuck (due to the sheer volume of the O.C.T.), but if the excess O.C.T. flows down the sides of the embedding head and bonds thereto, problems associated with separation of the tissue sample and O.C.T. from the embedding head may be aggravated when this O.C.T. freezes in the form of icicles. So dealing with the problems of attaching the chuck to the tissue and rapidly freezing the O.C.T. on the embedding head can cause additional problems when the time comes to remove the chuck, tissue sample, and O.C.T. from the embedding head. Thus, timing and the skill of the operator (whether a surgeon or a technician) becomes critically important to the tenth method.

Although problems associated with detachment of the tissue sample from the tissue chuck (when the surgeon attempts to forcibly break away the frozen tissue sample and O.C.T. from the embedding head) can be addressed by wiping a film of oil (such as petroleum jelly) on the embedding head prior to flattening the bowl-shaped surface thereto, this obviously makes it more difficult to get the tissue to adhere to the embedding head in the first place since the purpose of the oil is to reduce the tendency of the tissue sample to adhere to the embedding head. In addition, it adds one more step to the tissue sample preparation, since the embedding head must be re-oiled for each tissue sample. (Of course, if the embedding head becomes nicked or scratched during the course of normal use, this separation problem will be further aggravated.)

Most importantly, any method of preparing tissue samples which requires forcibly separating the flattened, formerly bowl-shaped surface of the tissue sample from the object to which it is adhered has the inherent risk that, when the tissue sample is separated therefrom, the very cancer cells which the surgeon is searching for may remain adhered to that object, and therefore not appear on the tissue slices produced in the cryostat. The nature of cancer cells increases the likelihood for the occurrence of this problem, because cancer cells are delicate and friable, and have no significant structural support as compared to healthy skin tissue. Furthermore, any method which relies on warming of such object to release the formerly bowl-shaped surface of the tissue sample therefrom introduces the problems associated with cell lysis described above.

An eleventh method is disclosed in U.S. Pat. No. 4,752,347 issued to Rada on Jun. 21, 1988, which is hereby incorporated by reference. Rada discloses a method and apparatus in which a tissue sample is placed onto a polished disk platform and covered with a flexible plastic membrane, such as polyethylene plastic sheet material. A vacuum source is activated, which evacuates air from between the membrane and the platform, drawing the bowl-shaped surface of the tissue sample toward the platform. Liquid nitrogen is then used to freeze the tissue sample to the platform, and once the tissue sample is frozen to the platform, the membrane is peeled away from the platform and the tissue sample. In one embodiment, O.C.T. is applied to the platform on which the tissue sample is located and to a corrugated platform such as a tissue chuck. After the O.C.T. has partially solidified, the platforms are mated together and the O.C.T. is allowed to solidify. Then the platforms are forcibly separated, or heated if need be, to remove the tissue sample from the platform to which it was originally frozen and leave it frozen to the corrugated platform. Unfortunately, since the invention disclosed in Rada relies on heat or force to free the tissue sample from the platform to which it was originally mounted, it suffers from the same problems associated therewith and described above.

As those skilled in the art will readily appreciate, in order to obtain a perfect section (i.e. a tissue slice which includes the entire flattened, formerly bowl-shaped surface, including the epidermal periphery thereof) the plane in which the flattened, formerly bowl-shaped surface lies must be substantially parallel to the plane in which the cryostat knife moves relative to the tissue sample. For example, to obtain a perfect section having a thickness of only 5 micrometers from a tissue sample having a flattened, formerly bowl-shaped surface measuring 1 centimeter in diameter, the acute cutting angle between the flattened, formerly bowl-shaped surface and the plane in which the cryostat knife moves relative to the tissue sample must be less than 30 thousandths of a degree (i.e. the arctangent of $5 \times 10^{-6}/1 \times 10^{-2}$). For tissue samples having a larger diameter, the angle must be even less. The relatively low percentages of perfect sections produced by the prior art indicate that none consistently provides a cutting angle within the acceptable tolerance.

Adjustable chuck fixtures are available within most cryostats to assist orientation of the planar surface in those situations where initially the planar surface is not parallel to the path of relative movement between the cryostat knife and the tissue sample. However, adjustable fixtures are expensive, and adjustment of the fixture can be dangerous due to the close proximity of the cryostat knife. Further, the fixture must still be adjusted to be within the cutting angle tolerance described above, and adjusting the fixture to the correct orientation is an iterative process that can consume a considerable amount of time. Adjusting the fixture to an angle for a specific tissue sample means that the next tissue sample will likely require adjustment of the fixture as well. If done incorrectly, this may require evaluation of many subsequent slices in order to view all of the formerly bowl-shaped surface.

Cryostats are generally designed such that when the chuck is placed within a chuck fixture within the cryostat, the tissue mounting surface of the chuck is parallel to the path of relative movement between the cryostat knife and the chuck. Therefore, as long as the planar surface is parallel to the path of relative movement between the cryostat knife and the tissue sample, the first slice should be the only section that need be evaluated. Unfortunately, despite the various methods and devices disclosed in the prior art to assist in obtaining a perfect tissue section, the problem persists.

What is needed is a quick, inspectable means and method of mounting a tissue sample to a cryostat chuck such that the planar, formerly bowl-shaped surface is consistently parallel to the tissue mounting surface of the chuck, does not require forcible removal of the tissue sample from an object or warming of the object to obtain separation of the tissue sample therefrom, and which does not require the timing or level of operator skill required by the prior art.

SUMMARY OF THE INVENTION

It is therefore an object of the present invention to provide an improved apparatus for preparing tissue samples for sectioning by a cryostat.

Another object of the present invention is to provide an apparatus which precisely orients tissue samples for optimum sectioning.

Another object of the present invention is to provide for visual inspection of the flattened bowl-shaped surface of the tissue sample prior to contact with the O.C.T. compound.

Another object of the present invention is to provide an apparatus which facilitates manipulation of the tissue sample for optimum sectioning.

Another object of the present invention is to provide an apparatus which is time and cost effective, so as to reduce the overall surgical time and expense necessary to effect the total excision of a malignancy.

Another object of the present invention is to provide an apparatus which is relatively simple to use, economical to manufacture, and particularly well adapted for the proposed usage thereof.

Another object of the present invention to provide an improved method for preparing tissue samples for sectioning by a cryostat.

According to the present invention, an apparatus for mounting a tissue specimen on a chuck for sectioning in a cryostat is disclosed, which apparatus comprises a base, a clamp for receiving a glass tissue preparation slide, a chuck holder secured to the base for holding the chuck in a predetermined orientation relative to the clamp, a support secured to the base and extending therefrom and terminating in a distal end, and, means for slideably securing said clamp to said support. The clamp is positionable between a first location in which the clamp is at a minimum distance from the chuck holder and a second location in which the clamp is at a maximum distance from the chuck holder. Additionally, the present invention discloses a method for mounting a tissue specimen on a tissue mounting surface of a tissue chuck for sectioning in a cryostat or the like comprising providing a chuck holder for holding the tissue mounting surface of the chuck essentially parallel to a primary reference plane. The primary reference plane is defined by primary arms of a clamp that is slideably moveable with respect to the chuck holder without changing the relative orientation of the chuck holder to the primary reference plane. The chuck is secured into the chuck holder such that the tissue mounting surface of the chuck is substantially parallel to the primary reference plane, and a puddle of tissue mounting fluid is placed on the tissue mounting surface of the chuck. A surface of the tissue specimen to be sectioned is then frozen to one face of a glass tissue preparation slide, and the glass tissue preparation slide is received within the clamp such that the one face is parallel to the primary reference plane. The clamp is then slid towards the chuck holder until the tissue sample is immersed in the tissue mounting fluid, and coolant is then sprayed on the slide, freezing the tissue mounting fluid to the tissue mounting surface of the chuck, the one face of the slide, and the tissue sample. The slide is then removed from the tissue sample and frozen tissue mounting fluid.

The foregoing and other features and advantages of the present invention will become more apparent from the following description and accompanying drawings.

BEST MODE FOR CARRYING OUT THE INVENTION

Figure 1:
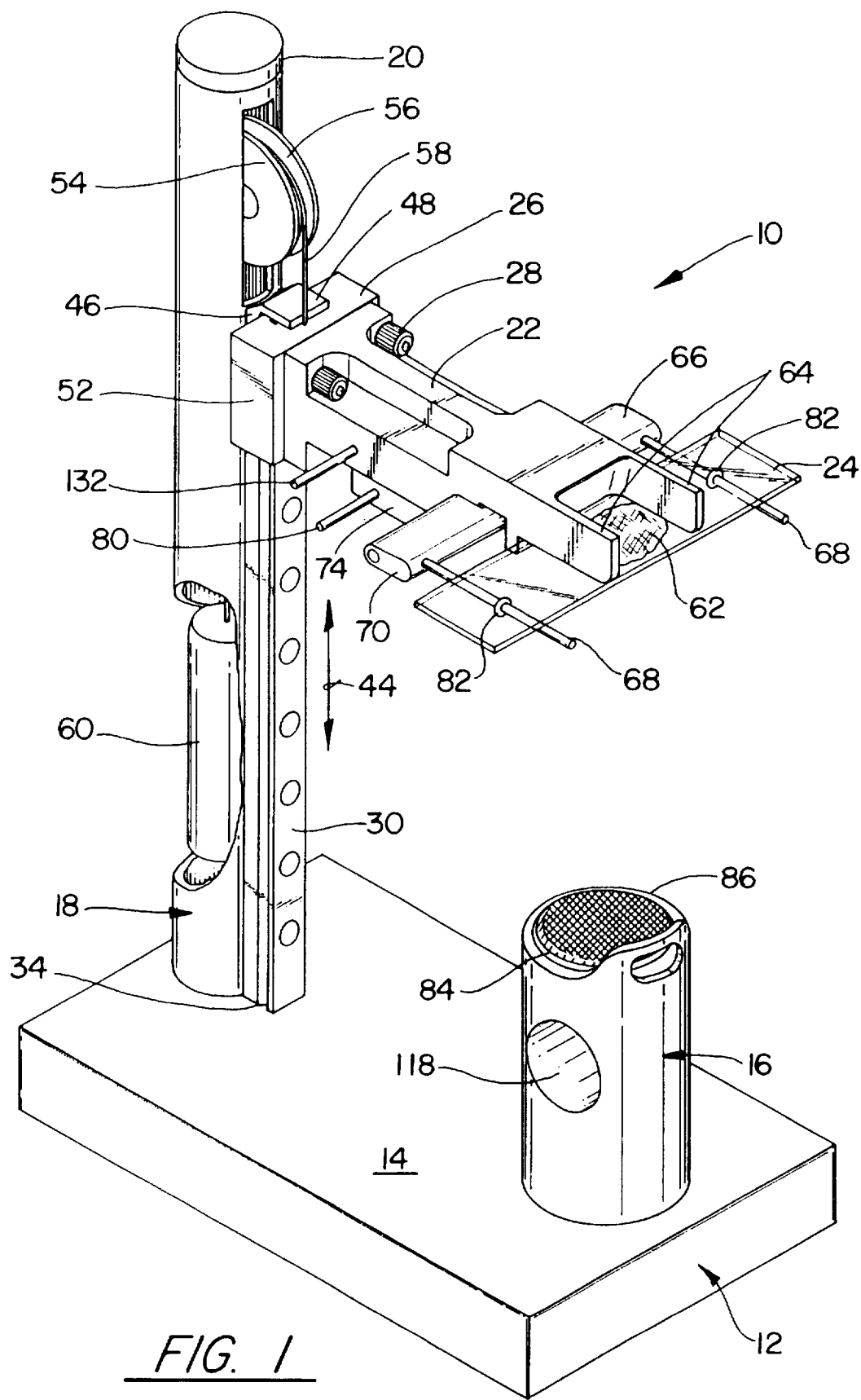
FIG. 1 is a perspective view of the apparatus of the present invention, showing a cut-away view of the support.

The apparatus 10 of the present invention as shown in FIG. 1 includes a base 12 having a planar base surface 14, to which is secured a chuck holder 16 and a hollow clamp support 18. The support 18 extends from the base surface 14 and terminates in a distal end 20. The present invention further includes a clamp 22 for receiving a tissue preparation slide 24 of the type known in the art and typically made of glass. The tissue mounting slide has two faces 25,27 which are parallel to each other, and an edge 29 which defines the perimeter of the two faces 25,27.

Figure 2:
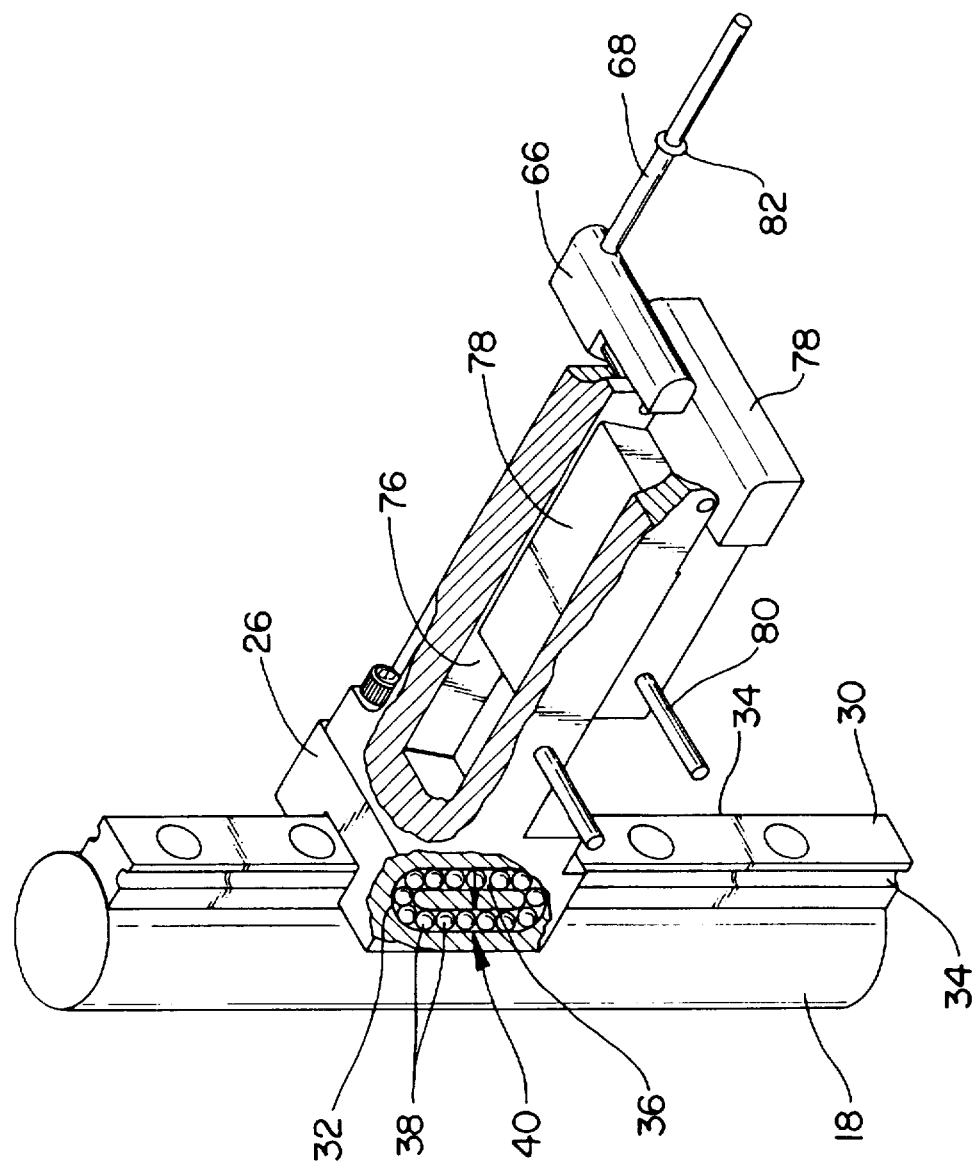
FIG. 2 is a perspective view of the support, and conveyor block of the present invention, showing a cut-away view of one of the loop paths.

The clamp 22 is fixedly secured to a conveyor block 26, preferably by bolts 28 which extend through holes (not shown) in the clamp 22 that are slightly larger than that diameter which would be necessary to simply accommodate the shaft of the bolt 28 extending therethrough. This slightly larger diameter allows for minor adjustments in the relative orientation between the clamp 22, and both the conveyor block 26 and the chuck holder 16. A rail 30 that is perpendicular to the base surface 14 is fixedly secured to the support 18 by bolts, screws or other manner known in the art, and the conveyor block 26 is movably secured to the rail 30. As shown in FIG. 2, in the preferred embodiment of the present invention the conveyor block 26 has two internal loop paths 32, and the rail 30 has two longitudinally extending rail grooves 34 on opposite sides of the rail 30. (Although only one of the loop paths 32 and one of the rail grooves 34 is shown in FIG. 2, it is to be understood that the conveyor block 26 and rail 30 are symmetric about the length of the rail 30.) Each of the loop paths 32 is located adjacent one of the rail grooves 34, and a portion of each loop path 32 is parallel to, and opens into, the groove 34 adjacent thereto.

The open portion of each loop path 32 constitutes a loop groove 36 which has the same dimensions, and opposes the rail groove 34 adjacent thereto. Ball bearings 38 having diameters only slightly less than the minimum width 40 of each loop path 32 are located therein, and the quantity of ball bearings 38 is such that the portion of each loop path 32 which is open to the rail groove 34 adjacent thereto is substantially filled with ball bearings 38 along the length thereof. Thus, as the conveyor block 26 moves along the rail 30, each ball bearing 38 rolling in each loop path 32 rolls into the open portion thereof and into the adjacent rail groove 34, rolls in the rail groove 34 along the length of the loop groove 36, and then rolls back into the closed portion of the loop path 32.

Each loop path 32 contains a sufficient quantity of ball bearings 38 such that the portion of each loop path 32 between the rail groove 34 and the loop groove 36 always has ball bearings 38 extending substantially along the entire length thereof, thereby interlocking the conveyor block 26 and the rail 30. Additionally, the gap 42 between each rail groove 34 and the adjacent loop groove 36 opposed thereto is sized such that the gap 42 is essentially equal to the diameter of the ball bearings 38. As those skilled in the art will readily appreciate, such a design allows the conveyor block 26 to move freely along the rail 30, but provides no degrees of freedom of rotation of the conveyor block 26 with respect the rail 30.

Figure 3:
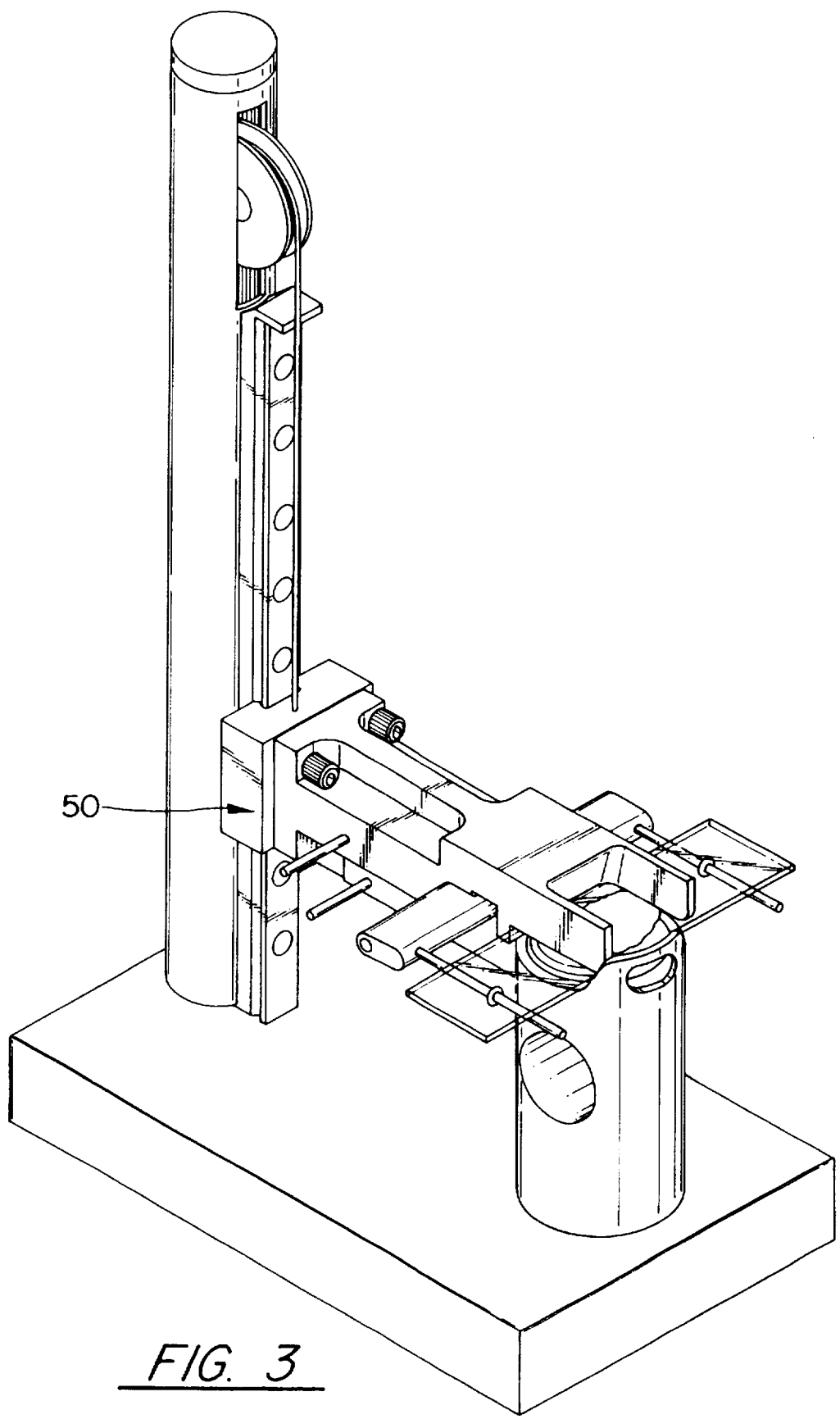
FIG. 3 is a perspective view of the apparatus of the present invention, showing the clamp at the first location and a partially cut-away view of the freezing chamber above the slide.
Figure 4:
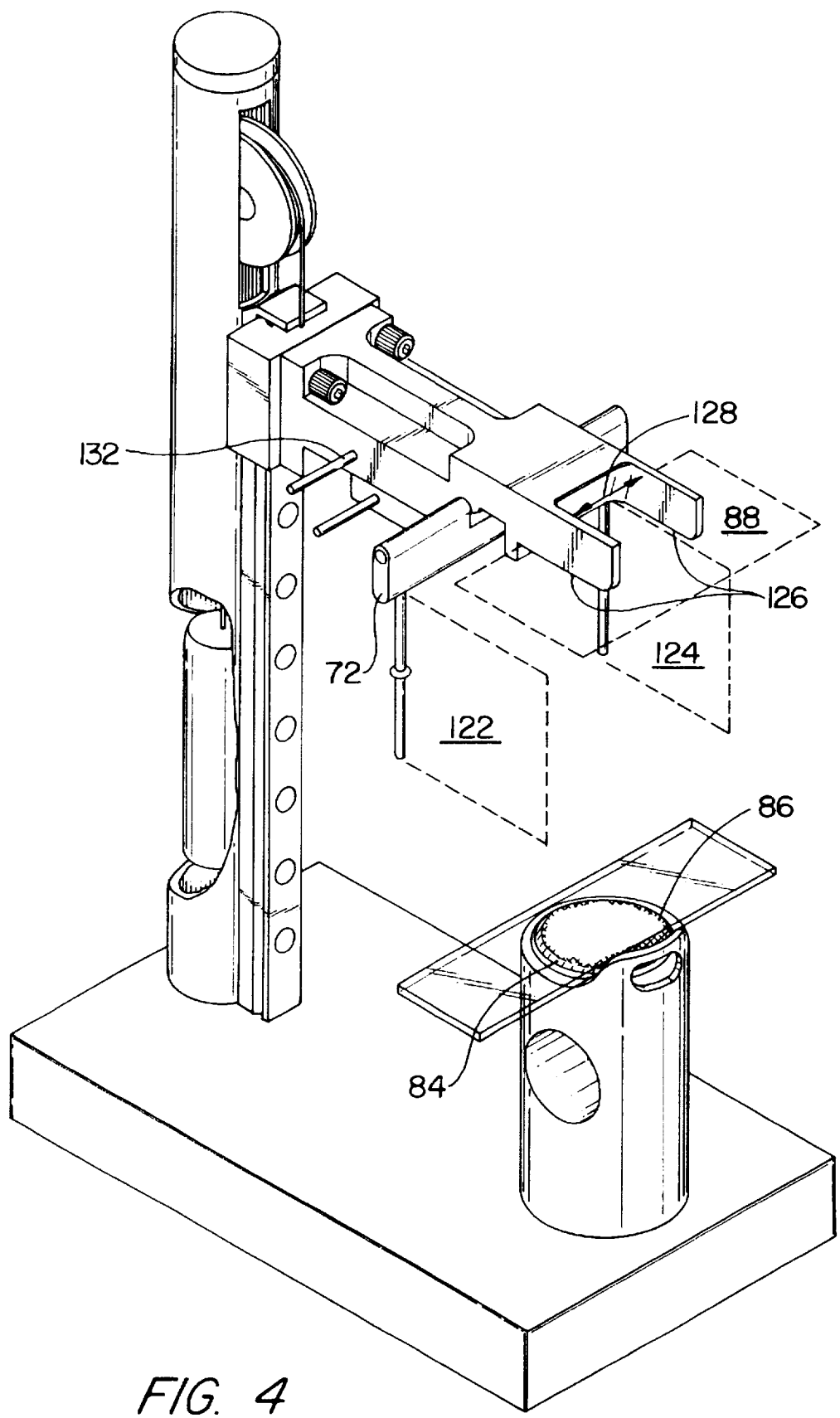
FIG. 4 is a perspective view of the apparatus of the present invention, showing the clamp at the second location.

Thus the conveyor block 26 is slideably secured to the support 18 by the rail 30 and constrained thereby to travel along a linear path 44 that is perpendicular to the base surface 14, while the conveyor block 26 and the ball bearings 38 therein cooperate with the rail grooves 34 to prevent rotation of the block 26 relative to the rail 30. At the end 46 of the rail 30 opposite the base 12, a stop 48 is provided to prevent the conveyor block 26 from sliding off that end 46. The clamp 22 is thus positionable between a first location 50, as shown in FIG. 3, in which the clamp 22 is at a minimum distance from the chuck holder 16, (and may in fact be in contact therewith), and a second location 52 in which the conveyor block 26 contacts the stop 48 and the clamp 22 is at a maximum distance from the chuck holder 16, as shown in FIGS. 1 and 4.

In the preferred embodiment of the present invention, a pulley 54 having an annular channel 56 therein is rotatably mounted in the support 18 adjacent the distal end 20. A cable 58 received within the channel 56 has a first end connected to the conveyor block 26, and a second end connected to a counterweight 60 that is suspended within the hollow support 18. Consequently, the counterweight 60 provides a predetermined force which acts on the clamp 22, through cable 58 and the conveyor block 26, to provide a predetermined force acting on the clamp 22 which tends to move the clamp 22 from the first location 50 to the second location. In the preferred embodiment of the present invention, the counterweight 60 is substantially equal to the combined weight of the conveyor block 26, the clamp 22, the bolts 28 that secure the clamp 22 to the conveyor block 26, and a typical glass microscope slide 24 with a tissue sample 62 secured thereto. Thus, once the slide 24 is released from the clamp 22, as described herein below, the weight of the counterweight 60 exceeds the combined weight of the conveyor block 26, the clamp 22, the bolts 28.

Referring again to FIG. 1, the clamp 22 of the present invention includes two primary arms 64 in spaced relation to each other and extending away from the conveyor block 26. These primary arms 64 are fixed relative to the conveyor block 26, and preferably are integral with the portion of the clamp 22 which is bolted to the conveyor block 26. Referring to FIG. 3, a wall 37 extends between the primary arms 64, as does a hood 39 which extends away from the wall 37 and is integral with the primary arms 64. The wall 37 has a terminal edge 41 which is integral with a land 43. A slide stop 35 extends from the land 43 adjacent to each of the primary arms 64 to aid in proper positioning of the microscope slide 24, as described below. The wall 37 is preferably offset from each slide stop 35 by ⅛ to ¼ of an inch, so that when a slide 24 is positioned within the clamp 22 against the slide stops 35, the slide 24, primary arms 64, wall 37, and hood 39 form a swirl pocket 45 immediately adjacent the slide 24.

Referring back to FIG. 1, the clamp 22 further includes a hinge 66 below the primary arms 64, and two secondary arms 68, in spaced relation to each other, are secured to the hinge 66. Thus, the hinge 66 provides for rotation of the secondary arms 68 relative to the conveyor block 26, such that the secondary arms 68 are rotatable between a first position 70 proximate the primary arms 64, as shown in FIG. 1, and a second position 72 distant therefrom at which the arms may be parallel to the rail 30, as shown in FIG. 4.

Figure 5:
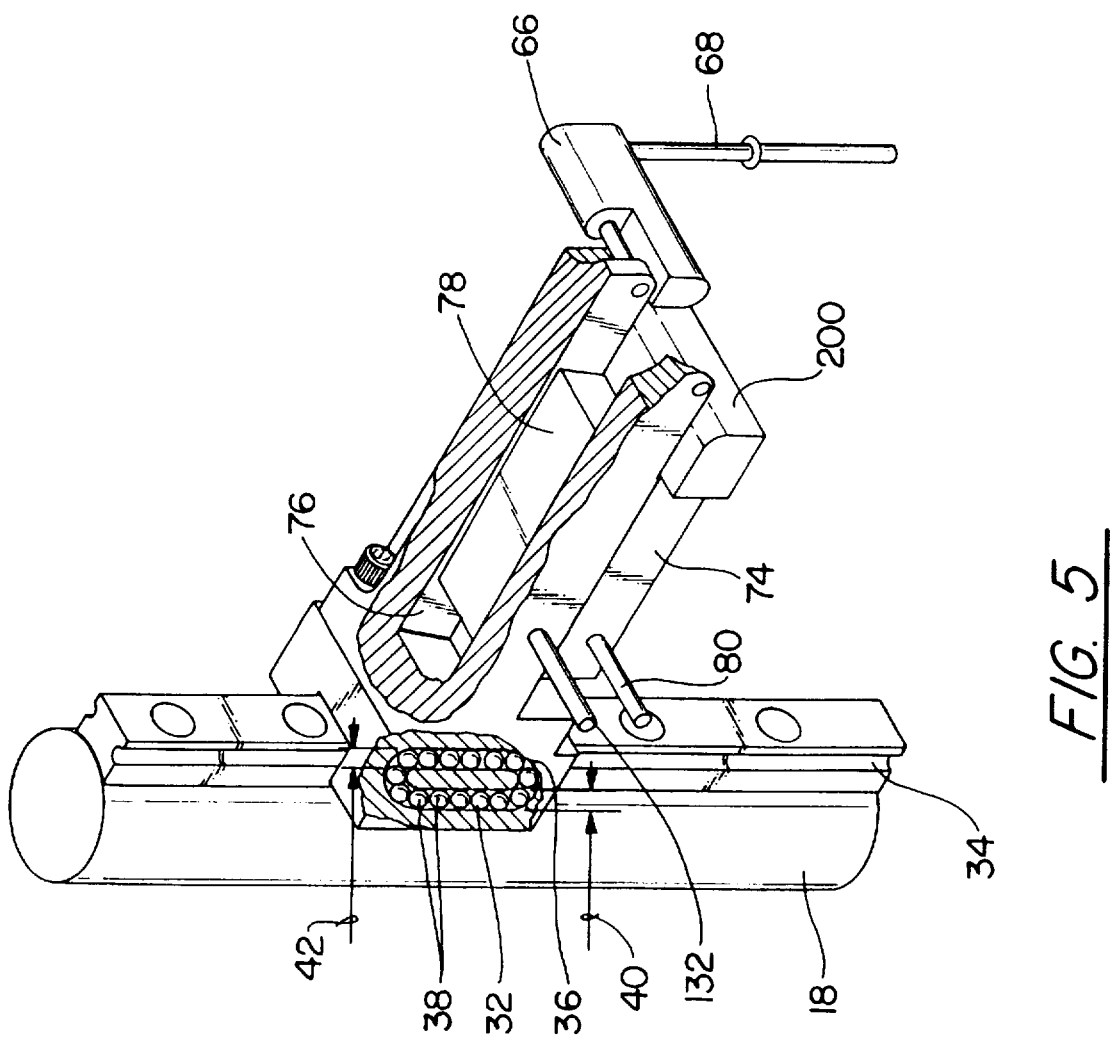
FIG. 5 is the perspective view of FIG. 2, showing the hinge support in a retracted position.
Figure 6:
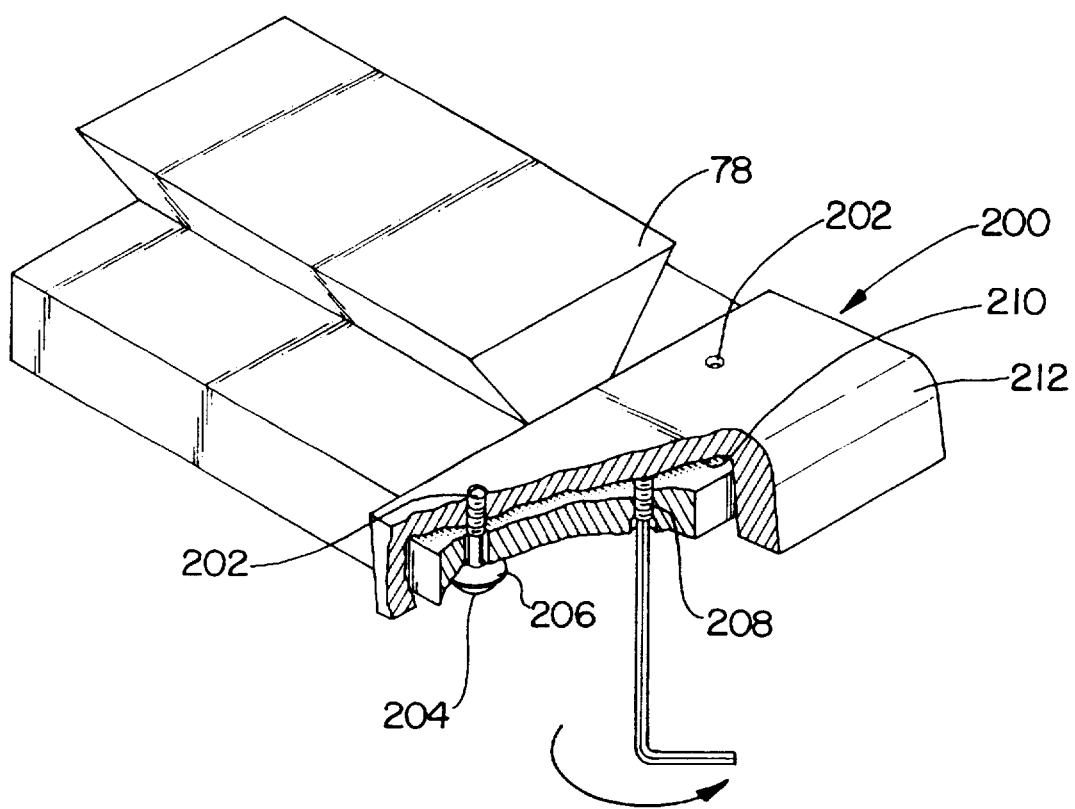
FIG. 6 is a partial cut-away view of the adjustable bearing cap of the present invention.

The clamp 22 has a locking mechanism 74 therein for locking the secondary arms 68 in the first position 70 (proximate the primary arms 64) for the purpose of clamping a microscope slide 24 between the primary and secondary arms 64,68. The locking mechanism 74, shown in cross-section in FIGS. 2 and 5, comprises a dovetail slot 76 in the clamp 22 extending away from the block 26, and a dovetail hinge support 78 slideably received in the dovetail slot 76. A positioning handle 80 is provided to facilitate selective positioning of the dovetail hinge support 78. As shown in FIG. 2, by sliding the dovetail hinge support 78 away from the support 18, the dovetail hinge support 78 is positionable relative to the hinge 66 so as to prevent rotation of the secondary arms 68 away from the primary arms 64, thus locking the secondary arms 68 in place. Conversely, as shown in FIG. 5, by sliding the dovetail hinge support 78 toward the support 18, the dovetail hinge support 78 is positionable relative to the hinge 66 so as to allow rotation of the secondary arms 68 away from the primary arms 64. As shown in FIG. 6, an adjustable bearing cap 200 is attached to one end of the dovetail hinge support 78. The bearing cap 200 is secured to the dovetail hinge support 78 by two small screws 202 which are threaded into the cap 200 but are not threaded into the dovetail hinge support 78. Sandwiched between the head 204 of each screw 202 and the dovetail hinge support 78 is an "O-ring" 206 made of neoprene or a similar material to allow the cap 200 to be tilted slightly with respect to the dovetail hinge support 78. A third screw 208, which is preferably an allen head screw, is threaded into the dovetail hinge support 78 but does not extend into the bearing cap 200. Instead, the third screw 208 bears on the underside 210 of the bearing cap 200, such that advancing the third screw 208 raises the leading edge 212 of the bearing cap 200. This adjustable feature of the bearing cap 200 allows for increasing or decreasing interference between the bearing cap 200 and the hinge 66 through adjustment of the relative position of the bearing cap 200 to the hinge 66 which compensates for any wear which might occur due to rubbing of the bearing cap 200 against the hinge 66.

Each of the secondary arms 68 preferably includes an "O-ring" 82 made of neoprene or a similar material to act both as a cushion between the secondary arms 68 and the microscope slide 24, and to provide a frictional force to hold the slide 24 securely in place when the clamp 22 is in the locked position, as shown in FIG. 1.

The chuck holder 16 serves the purpose of holding a cryostat chuck 84 in a predetermined orientation relative to the clamp 22, such that as shown in FIG. 4, the mounting surface 86 of the chuck 84 is essentially parallel to a primary reference plane 88 described in greater detail below. It is to be understood that the mounting surface 86 of the chuck 84 is textured or grooved to maximize the adherence of the tissue sample 62 to the mounting surface 86, and that therefore the mounting surface 86 is not actually planar. Accordingly, the term "essentially parallel to the primary reference plane 88" as used herein means that the mounting surface 86, excluding such texturing, lies within a plane that is substantially parallel to the primary reference plane 88. As those skilled in the art will readily appreciate, the presence of the "O-rings" 82 ensure that when a slide 24 is secured in the clamp 22, the slide 24 will be parallel to the primary reference plane 88 even if the secondary arms 68 are not exactly parallel to the primary arms 64.

Figure 7:
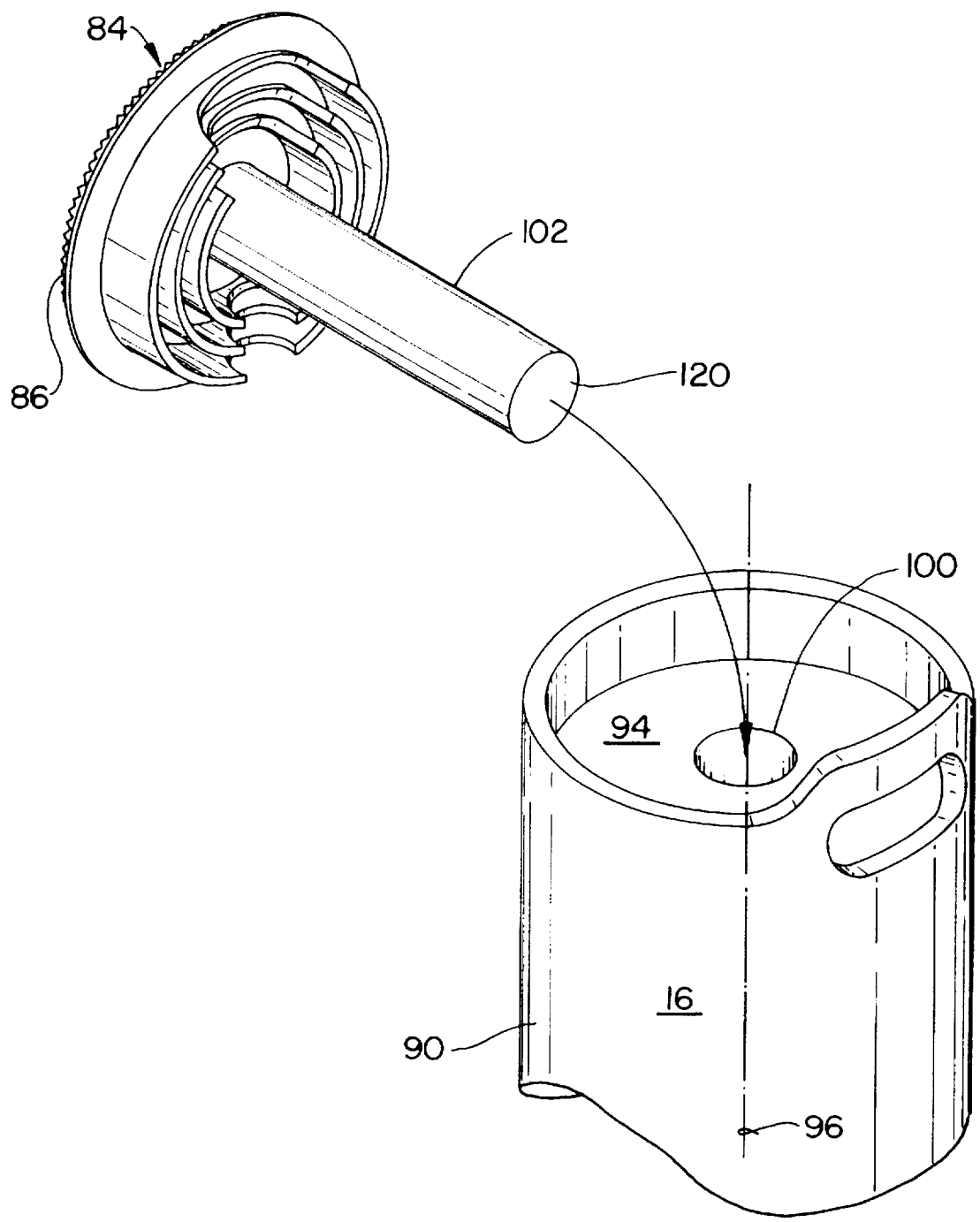
FIG. 7 is a perspective view of the tissue chuck and chuck holder used in the present invention.

Referring now to FIG. 7, the chuck holder 16 preferably is a solid cylinder 90 of rigid material having a coefficient of heat transfer less than most metals. A shaft hole 100, which has a diameter sized to receive the shaft 102 of the chuck 84, extends from the upper surface 94 of the chuck holder 16 along the centerline 96 thereof, which is parallel to the rail 30. The diameter of the upper surface 94 is preferably smaller than the diameter of the tissue mounting surface 86 of the chuck 84 to facilitate removal of the chuck 84 from the chuck holder 16. The chuck 84 typically includes a lip 300 made of a material such as neoprene to allow for easier, and more comfortable, handling of the chuck 84 when it has been cooled to sub-freezing temperatures. An orifice 118 in the chuck holder 16, as shown in FIG. 1, intersects the shaft hole 100 to provide access to the end 120 of the shaft 102 within the chuck holder 16 for the purpose of facilitating removal of the chuck 84 from the chuck holder 16 by pressing upwards on the end 120 of the shaft 102. This orifice 118 is appropriately sized so as to permit insertion of a thumb or finger.

Referring again to FIG. 4, rotation of the secondary arms 68 defines two secondary reference planes 122,124, and the chuck holder 16 is located between the secondary reference planes 122,124. Thus, rotation of the secondary arms 68 is not subject to interference with the chuck holder 16. Each of the primary arms 64 has a lower surface 126 facing the base 12, and together the lower surfaces 126, the terminal edge 41, and the land 43, as shown in FIG. 3, all lie in the same plane and define the primary reference plane 88. The primary reference plane 88 is perpendicular to the linear path 44 along which the conveyor block 26 is constrained to travel. As those skilled in the art will readily appreciate, since the microscope slide has two faces 25,27 which are parallel to each other, and one face 27 of the slide lies flush against the lower surfaces 126 of the primary arms 64 when the slide 24 is received within the clamp 22, both faces 25,27 are parallel to the primary reference plane 88 when the slide 24 is received within the clamp 22. Therefore, the clamp 22 is positionable between the first location 50 and a second location 52, and both faces 25,27 of the tissue mounting slide 24 are substantially parallel to the tissue mounting surface 86 of the chuck 84 at the first location 50, the second location 52, and all locations therebetween. Additionally, the primary arms 64 of the clamp 22 are slideably moveable with respect to the chuck holder 16 without changing the relative orientation of the primary arms 64 to the chuck holder 16.

Preferably the primary arms 64, as shown in FIG. 4, are centered over the chuck holder 16 and the spacing 128 between the primary arms 64 is less than the diameter of the mounting surface 86 of the chuck 84 in the chuck holder 16, so that movement of the clamp 22 towards the chuck holder 16 necessarily ceases when the primary arms 64 contact the mounting surface 86 of the chuck 84 when no slide 24 is present in the clamp 22, and when a slide 24 is present in the clamp 22, the interaction of the primary arms 64 and the mounting surface 86 of the chuck 84 does not produce a significant bending moment in the slide 24 and thereby cause breakage of the slide 24.

Figure 8:
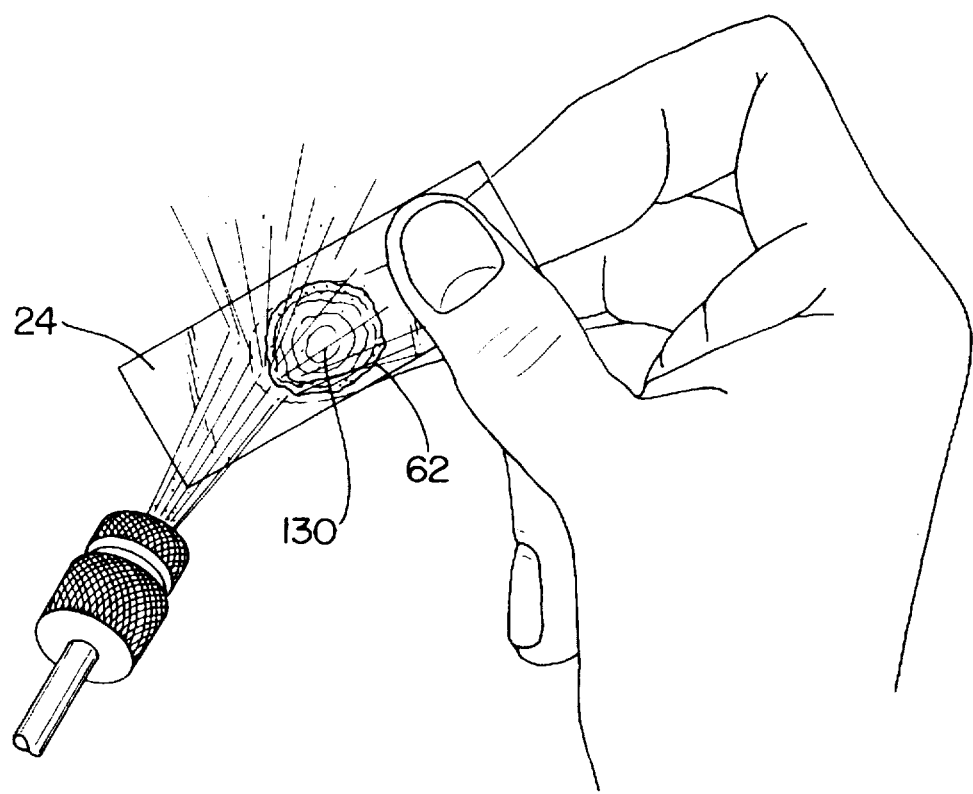
FIG. 8 shows a tissue sample being frozen to a microscope slide for use with the apparatus of the present invention.

In operating the apparatus of the present invention, the clamp 22 is raised away from the chuck holder 16 and a chuck 84 is placed therein. The surgeon excises the skin tumor from the patient using the Mohs technique described above, producing a tissue sample 62 having a bowl-shaped surface 130. As shown in FIG. 8, the bowl-shaped surface 130 is pressed onto one face of a glass microscope slide 24 while a coolant such as liquid nitrogen is sprayed on the opposite face of the slide 24. As the bowl-shaped surface 130 is pressed against the nitrogen chilled slide 24, the bowl-shaped surface 130 freezes to the slide 24. By judiciously working around the periphery of the tissue sample 62 while pressing the sample 62 against the slide 24 (and intermittently spraying the opposite side of the slide 24 with nitrogen to maintain the slide 24 below freezing temperature), the entire bowl-shaped surface 130 can be frozen to the slide 24, thus flattening the surface which had been bowl-shaped. Because the surgeon can directly view the bowl-shaped surface of the sample 62 as the surgeon is freezing the sample 62 to the slide, the surgeon can ensure that the bowl-shaped surface does not become creased as it is pressed against the slide 24 and that no air bubbles become trapped between the sample 62 and the slide 24.

A small puddle of O.C.T. or similar tissue mounting fluid is deposited at the center of the mounting surface 86 of the chuck 84. With the surface of the slide 24 on which the tissue sample 62 is mounted facing the chuck 84 as shown in FIG. 1, the microscope slide 24 is then positioned against the lower surfaces 126 of the primary arms 64 and slid towards the rail 30 until the slide 24 contacts each of the slide stops 35. Using the positioning handle 80, the surgeon raises the secondary arms 68 into contact with the slide 24 by extending the dovetail support 78 from the dovetail slot 76 until the dovetail support 78 moves bearing cap 200 so that bearing cap 200 contacts and rotates the hinge 66 into the position at which the secondary arms 68 swing up and contact the slide 24, sandwiching the slide 24 between the primary and secondary arms 64,68. If necessary, the slide 24 is adjusted to center the tissue sample 62 over the puddle of O.C.T., and the dovetail support 78 is extended slightly further to support the hinge 66 and prevent the secondary arms 68 from rotating away from the primary arms 64.

As those skilled in the art will readily appreciate, since the slide 24 is flat, and the mounting surface 86 of the chuck 84 is parallel to the primary reference plane 88 defined by the lower surfaces 126 of the primary arms 64, clamping the slide 24 firmly against the lower surfaces 126 of the primary arms 64 necessarily positions the lower face 25 of the slide 24 in a plane that is substantially parallel to the plane in which the tissue mounting surface 86 of the chuck 84 is located. During the process that follows, liquid nitrogen may be sprayed onto the upper surface of the slide 24 (into the swirl pocket 45 between the primary arms 64) as needed to keep the tissue sample 62 frozen to the slide 24.

As shown in FIG. 3, the slide 24 is lowered into contact with the O.C.T. fluid on the mounting surface 86 of the chuck 84, so that the tissue sample 62 is immersed in the O.C.T. Coolant such as liquid nitrogen is then sprayed into the swirl pocket 45 until the O.C.T. freezes. As those skilled in the art will readily appreciate, since the slide 24 is being held firmly against the land 43 and the lower surface 126 of each of the primary arms 64, as long as the coolant is sprayed directly into the pocket 45, no splattering of the O.C.T. will occur as a result of the coolant spray, since the slide 24 shields the O.C.T. from the blast of the coolant spray.

Once the tissue sample 62 has been frozen to the mounting surface 86 of the chuck 84, the secondary arms 68 are rotated downward to clear the slide 24 as shown in FIG. 4, by retracting the dovetail support 78 into the dovetail slot 76 until the bearing cap 200 of the dovetail support 78 no longer contacts the hinge 66. The entire clamp 22 is then moved up and away from the slide 24 by a gentle upward tap on the clamp pin 132. The chuck 84, with attached tissue sample 62 and slide 24, can then be removed from the chuck holder 16 by reaching into the second orifice 118 of the chuck holder 16 with a finger and pressing upward on the end 120 of the chuck shaft 102. Further spraying of the slide 24 with liquid nitrogen causes the slide 24 to release from the sample 62 due to the relative differences in the coefficients of thermal expansion between the glass slide 24 and the water-based tissue sample 62. Thus, the tissue sample 62 is freed from the slide 24 without thawing the sample 62 or forcibly removing it therefrom, thereby avoiding the problems discussed above associated with these methods of releasing the sample 62 from the object to which it is attached. The resulting tissue sample 62 is frozen to the chuck 84 such that the formerly bowl-shaped surface is now parallel to the mounting surface 86 of the chuck 84. The chuck 84 can then be placed in a cryostat, and the tissue sample 62 sliced parallel to the mounting surface 86, sectioning the entire formerly bowl-shaped surface, including the peripheral edge thereof, with a single slice of the cryostat knife.

As those skilled in the art will readily appreciate, the first or second slice of tissue will produce a section of the tissue sample 62 that, through examination under a microscope, will indicate whether the tumor has spread beyond the tissue sample 62. Accordingly, the surgeon can quickly determine whether additional tissue must be removed to excise all of the tumor.

The present invention provides a quick, inspectable means and method of mounting a tissue sample to a cryostat chuck such that the planar, formerly bowl-shaped surface is consistently parallel to the tissue mounting surface of the chuck. Additionally, the present invention does not require the application of force or heat to the tissue sample to obtain removal of the tissue sample from the object to which it has been frozen. As a result, the present invention does not require the timing or level of operator skill required by the prior art to obtain consistently perfect tissue sections.

Although this invention has been shown and described with respect to detailed embodiments thereof, it will be understood by those skilled in the art that various changes in form and detail thereof may be made without departing from the spirit and scope of the claimed invention.

I claim:

1. An apparatus for mounting a tissue specimen on a tissue mounting surface of a tissue chuck for sectioning in a cryostat, said apparatus comprising:

a base;

a clamp for receiving a glass tissue preparation slide having at least one face;

a chuck holder secured to said base for holding said tissue mounting surface of said chuck in a predetermined orientation relative to said clamp;

a support secured to said base and extending therefrom and terminating in a distal end; and, means for slideably securing said clamp to said support comprising a rail fixedly secured to said support, a conveyor block movably secured to said rail and constrained by said rail to travel along a linear path, said block including means for preventing rotation of said block relative to said rail, said block fixedly secured to said clamp; and, means for providing a predetermined force acting on said clamp, comprising a pulley rotatably mounted adjacent said distal end and having an annular channel therein, a cable having a first end connected to said clamp and a second end connected to a counterweight, said cable received within said channel, said predetermined force tending to move said clamp from said first position to said second position;

wherein said clamp is positionable between a first location in which the clamp is at a minimum distance from said chuck holder and a second location in which the clamp is at a maximum distance from said chuck holder, and said one face of said tissue mounting slide is substantially parallel to said tissue mounting surface of said chuck at said first location, said second location, and all locations therebetween.

2. The apparatus of claim 1 wherein said clamp comprises at least one first arm extending away from said block, said first arm fixed relative to said block, at least one second arm, a hinge, said second arm secured to said hinge, said hinge providing for rotation of said second arm relative to said block, said one second arm rotatable between a first position proximate said first arm and a second position distant therefrom, and means for locking said one second arm in said first position.

3. The apparatus of claim 2 wherein said means for locking said second arm in said first position comprise a slot extending away from said block, a hinge support slideably received in said slot, said hinge support positionable relative to said hinge so as to prevent rotation of said second arm.

4. The apparatus of claim 3 wherein said hinge support includes an adjustable bearing cap which is selectively adjustable to increase or decrease interference between the bearing cap and the hinge.

5. The apparatus of claim 2 wherein said clamp includes two first arms in spaced relation to each other, each of said first arms having a lower surface facing said base, said lower surfaces defining a first reference plane, and said first reference plane is perpendicular to said linear path.

6. The apparatus of claim 5 wherein said means for locking said second arm in said first position comprise a slot extending away from said block, a hinge support slideably received in said slot, said hinge support positionable relative to said hinge so as to prevent rotation of said second arm.

7. The apparatus of claim 6 wherein said hinge support includes an adjustable bearing cap which is selectively adjustable to increase or decrease interference between the bearing cap and the hinge.

8. The apparatus of claim 2 wherein said clamp includes two second arms in spaced relation to each other, and rotation of said second arms defines two second reference planes, and said chuck holder is located between said second reference planes.

9. The apparatus of claim 8 wherein said means for locking said one second arm in said first position comprise a slot extending away from said block, a hinge support slideably received in said slot, said hinge support positionable relative to said hinge so as to prevent rotation of said second arm.

10. The apparatus of claim 9 wherein said hinge support includes an adjustable bearing cap which is selectively adjustable to increase or decrease interference between the bearing cap and the hinge.

11. The apparatus of claim 8 wherein said clamp includes two first arms in spaced relation to each other, each of said first arms is located between said second reference planes, each of said first arms having a lower surface facing said base, said lower surfaces defining a first reference plane, and said first reference plane is perpendicular to said linear path.

12. The apparatus of claim 11 wherein said means for locking said one second arm in said first position comprise a slot extending away from said block, a hinge support slideably received in said slot, said hinge support positionable relative to said hinge so as to prevent rotation of said second arm.

13. The apparatus of claim 12 wherein said hinge support includes an adjustable bearing cap which is selectively adjustable to increase or decrease interference between the bearing cap and the hinge.

* * * * *